United States Patent [19]

Doehner, Jr.

[11] Patent Number: 5,283,335
[45] Date of Patent: Feb. 1, 1994

[54] HERBICIDAL 2-(2-IMIDAZOLIN-2-YL)-BENZO-(6-MEMBERED)-HETEROCYCLES

[75] Inventor: Robert F. Doehner, Jr., East Windsor, N.J.

[73] Assignee: American Cyanamid Company, Wayne, N.J.

[21] Appl. No.: 849,997

[22] Filed: Mar. 10, 1992

Related U.S. Application Data

[63] Continuation of Ser. No. 576,643, Aug. 31, 1990, abandoned.

[51] Int. Cl.⁵ .......................................... C07D 401/04
[52] U.S. Cl. .................................... 546/167; 504/247
[58] Field of Search ................... 71/92; 546/170, 167, 546/153, 155; 504/130, 247

[56] References Cited

U.S. PATENT DOCUMENTS

| | | | |
|---|---|---|---|
| 4,188,487 | 2/1980 | Los | 504/180 |
| 4,297,128 | 10/1981 | Los | 504/277 |
| 4,554,013 | 11/1985 | Los | 504/277 |
| 4,608,079 | 8/1986 | Los | 504/246 |
| 4,650,514 | 3/1987 | Los et al. | 504/246 |
| 4,752,323 | 6/1988 | Los et al. | 504/245 |
| 4,816,060 | 3/1989 | Steller et al. | 504/246 |
| 4,824,474 | 4/1989 | Numata et al. | 504/247 |
| 4,911,753 | 3/1990 | Los | 504/156 |

*Primary Examiner*—John M. Ford
*Assistant Examiner*—Matthew V. Grumbling
*Attorney, Agent, or Firm*—J. W. Hogan, Jr.

[57] ABSTRACT

There are provided o-carboxy-(5-oxo-2-imidazolin-2-yl)benzo-(6-membered)-heterocyclic compounds which contain one, two or three heteroatoms and derivatives thereof and a method for the use therewith to control monocotyledenous and dicotyledenous plant species.

1 Claim, No Drawings

HERBICIDAL 2-(2-IMIDAZOLIN-2-YL)-BENZO-(6-MEMBERED)-HETEROCYCLES

This is a continuation of co-pending application Ser. No. 07/576,643 filed on Aug. 31, 1990 now abandoned.

BACKGROUND OF THE INVENTION

Certain imidazolinyl benzoic and naphthoic acids, esters and salts and their use as herbicidal agents are described in U.S. Pat. Nos. 4,188,487; 4,297,128 and 4,554,013 and in patent applications GB 2 172 866 A and EP 86200304.3. However, the imidazolinyl benzoheterocycles of the present invention are not described nor suggested in said patents and patent applications. Fused heteropyridine compounds and their herbicidal use are described in U.S. Pat. Nos. 4,650,514 and 4,752,323 and copending U.S. application Ser. No. 465,569 filed on Jan. 16, 1990. Although a variety of herbicidally active imidazolinyl compounds are known, still more effective imidazolinyl compounds would be useful to farmers, agriculturalists, industrialists and the like for the control of undesirable plant species.

It is an object of the present invention to provide effective herbicidal imidazolinyl o-carboxy-2-benzoheterocyclic compounds and indoloheterocyclic diones for controlling a variety of monocotyledenous and dicotyledenous plant species such as those species which are generally difficult to control in agronomic practice.

SUMMARY OF THE INVENTION

The present invention relates to 2-(2-imidazolin-2-yl)benzoheterocyclic compounds having the structure

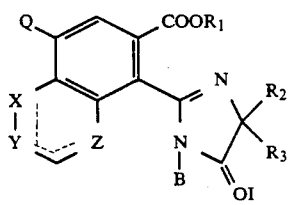
a.

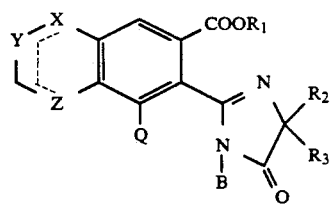
b.

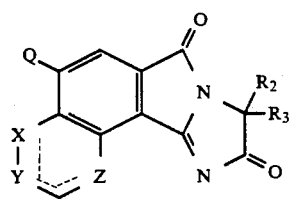
c.

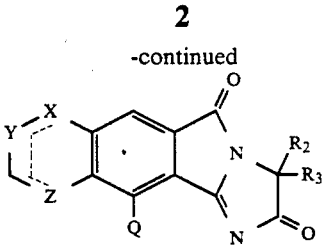
d.

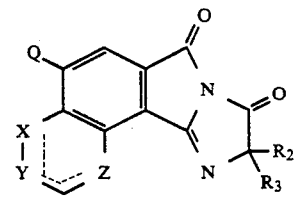
e.

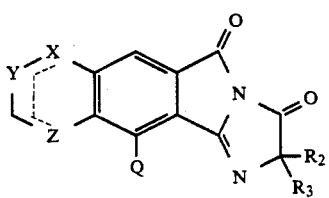
f.

wherein
$R_1$ is hydrogen, di($C_1$-$C_4$)alkylimino, $C_1$-$C_{12}$ alkyl optionally substituted with one to three of the following: $C_1$-$C_4$ alkoxy, $C_1$-$C_4$ alkylthio, halogen, hydroxy, $C_3$-$C_6$ cycloalkyl, benzyloxy, furyl, phenyl optionally substituted with one nitro, one to three halogens, $C_1$-$C_4$ alkyl groups or $C_1$-$C_4$ alkoxy groups, carboxy, $C_1$-$C_4$ alkoxycarbonyl, cyano or tri($C_1$-$C_4$)alkylammonium halide, $C_3$-$C_{12}$ alkenyl optionally substituted with one to three of the following: $C_1$-$C_4$ alkoxy, phenyl, halogen or $C_1$-$C_4$ alkoxycarbonyl, $C_3$-$C_6$ cycloalkyl optionally substituted with one to three $C_1$-$C_4$ alkyl groups, $C_3$-$C_{16}$ alkynyl optionally substituted with one to three halogens or a cation;

$R_2$ is $C_1$-$C_4$ alkyl;

$R_3$ is $C_1$-$C_4$ alkyl or $C_3$-$C_6$ cycloalkyl, and when $R_2$ and $R_3$ are taken together with the carbon to which they are attached they may represent $C_3$-$C_6$ cycloalkyl optionally substituted with methyl;

B is hydrogen, $COR_4$ or $SO_2R_5$ with the proviso that when B is $COR_4$ or $SO_2R_5$, $R_1$ is other than hydrogen or a cation;

$R_4$ is $C_1$-$C_{11}$ alkyl, chloromethyl or phenyl optionally substituted with halogen, nitro or $C_1$-$C_4$ alkyl;

$R_5$ is $C_1$-$C_4$ alkyl or phenyl optionally substituted with $C_1$-$C_4$ alkyl;

X, Y and Z are each independently $CR_6$, $CR_7R_8$, N, $NR_9$, O or S with the proviso that at least one of X, Y and Z must be N, $NR_9$, O or S and with the further proviso that when X is O or S, then Y must be $CR_6$, $CR_7R_8$, N or $NR_9$;

the ≡≡≡≡ configuration represents either a single bond or a double bond with the proviso that when any of X, Y or Z is $CR_7R_8$, $NR_9$, O or S, then the ≡≡≡≡ configuration attached thereto represents a single bond;

$R_6$, $R_7$ and $R_8$ are independently hydrogen, halogen, $C_1$-$C_4$ alkoxy or $C_1$-$C_4$ alkyl optionally substituted with one hydroxy or one to three halogens, $C_1-C_4$ alkoxy groups or $C_1-C_4$ alkylthio groups;

$R_9$ is hydrogen or $C_1-C_4$ alkyl optionally substituted with one hydroxy or one to three halogens, $C_1-C_4$ alkoxy groups or $C_1-C_4$ alkylthio groups;

Q is hydrogen, halogen, $C_1-C_4$ alkoxy or $C_1-C_4$ alkyl optionally substituted with one to three of the following: halogen, $C_1-C_4$ alkoxy, $C_1-C_4$ alkylthio or $C_2-C_4$ alkenyl;

the optical isomers thereof when $R_2$ and $R_3$ are not the same or when $R_7$ and $R_8$ are not the same;

the tautomers and geometric isomers thereof and the acid addition salts thereof except when $R_1$ is a salt-forming cation.

The present invention further provides processes for the preparation of the above-said compounds and methods for controlling undesirable monocotyledenous and dicotyledenous plant species therewith.

DESCRIPTION OF THE INVENTION

This invention relates to 2-(2-imidazolin-2-yl)benzoheterocyclic compounds having the structure

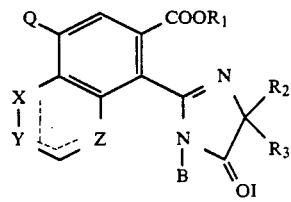  a.

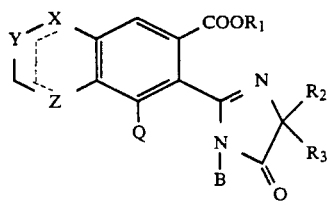  b.

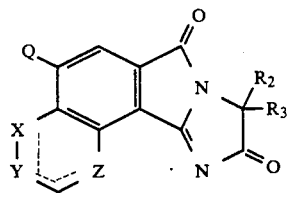  c.

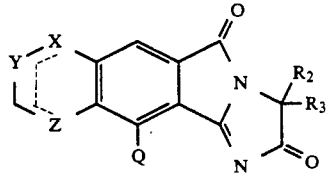  d.

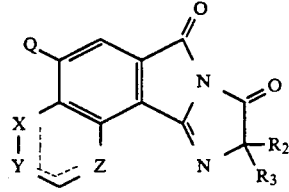  e.

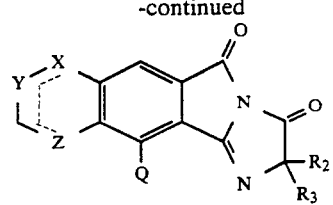  f.

wherein
$R_1$ is hydrogen, di($C_1-C_4$)alkylimino,
  $C_1-C_{12}$ alkyl optionally substituted with one to three of the following: $C_1-C_4$ alkoxy, $C_1-C_4$ alkylthio, halogen, hydroxy, $C_3-C_6$ cycloalkyl, benzyloxy, furyl, phenyl, optionally substituted with one nitro, one to three halogens, $C_1-C_4$ alkyl groups or $C_1-C_4$ alkoxy groups, carboxy, $C_1-C_4$ alkoxycarbonyl, cyano or tri($C_1-C_4$)alkylammonium halide,
  $C_3-C_{12}$ alkenyl optionally substituted with one to three of the following: $C_1-C_4$ alkoxy, phenyl, halogen or $C_1-C_4$ alkoxycarbonyl,
  $C_3-C_6$ cycloalkyl optionally substituted with one to three $C_1-C_4$ alkyl groups,
  $C_3-C_{16}$ alkynyl optionally substituted with one to three halogens or
  a cation;

$R_2$ is $C_1-C_4$ alkyl;

$R_3$ is $C_1-C_4$ alkyl or $C_3-C_6$ cycloalkyl, and when $R_2$ and $R_3$ are taken together with the carbon to which they are attached they may represent $C_3-C_6$ cycloalkyl optionally substituted with methyl;

B is hydrogen, $COR_4$ or $SO_2R_5$ with the proviso that when B is $COR_4$ or $SO_2R_5$, $R_1$ is other than hydrogen or a cation;

$R_4$ is $C_1-C_{11}$ alkyl, chloromethyl or phenyl optionally substituted with halogen, nitro or $C_1-C_4$ alkyl;

$R_5$ is $C_1-C_4$ alkyl or phenyl optionally substituted with $C_1-C_4$ alkyl;

X, Y and Z are each independently $CR_6$, $CR_7R_8$, N, $NR_9$, O or S with the proviso that at least one of X, Y and Z must be N, $NR_9$, O or S and with the further proviso that when X is O or S, then Y must be $CR_6$, $CR_7R_8$, N or $NR_9$;

the ═══ represents either a single bond or a double bond with the proviso that when any of X, Y or Z is $CR_7R_8$, $NR_9$, O or S, then the ═══ configuration attached thereto represents a single bond;

$R_6$, $R_7$ and $R_8$ are independently hydrogen, halogen, $C_1-C_4$ alkoxy or $C_1-C_4$ alkyl optionally substituted with one hydroxy or one to three halogens, $C_1-C_4$ alkoxy groups or $C_1-C_4$ alkylthio groups;

$R_9$ is hydrogen or $C_1-C_4$ alkyl optionally substituted with one hydroxy or one to three halogens, $C_1-C_4$ alkoxy groups or $C_1-C_4$ alkylthio groups;

Q is hydrogen, halogen, $C_1-C_4$ alkoxy or $C_1-C_4$ alkyl optionally substituted with one to three of the following: halogen, $C_1-C_4$ alkoxy, $C_1-C_4$ alkylthio or $C_2-C_4$ alkenyl;

the optical isomers thereof when $R_2$ and $R_3$ are not the same or when $R_7$ and $R_8$ are not the same;

the tautomers and geometric isomers thereof and the acid addition salts thereof except when $R_1$ is a salt-forming cation.

The ═══ configuration represents a double bond between X and Y when X or Y are N or $CR_6$. The ≈≈≈ configuration represents a double bond when attached to Z and Z is N or $CR_6$.

The term halogen designates F, Cl, Br or I. The term cation, as used in the present specification and claims, designates alkali metals, alkaline earth metals, manganese, copper, iron, zinc, cobalt, lead, silver, nickel, ammonium or organic ammonium. The alkali metals include sodium, potassium and lithium. Among the organic ammonium cations suitable for use in the present invention are monoalkylammonium, dialkyl ammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$–$C_6$ cycloalkylammonium, piperidinium, morpholinium, pyrrolidinium, benzylammonium and the like.

Among the o-carboxy-(5-oxo-2-imidazolin-2-yl)benzoheterocycles described in the present invention are o-(2-imidazolin-2-yl)benzopyrancarboxylates, o-(2-imidazolin-2-yl)benzodioxancarboxylates, o-(2-imidazolin-2-yl)benzoxazinecarboxylates, o-(2-imidazolin-2-yl)benzoxadiazinecarboxylates, o-(2-imidazolin-2-yl)benzodioxazinecarboxylates, o-(2-imidazolin-2-yl)benzothiopyrancarboxylates, o-(2-imidazolin-2-yl)benzothiazinecarboxylates, o-(2-imidazolin-2-yl)benzodithiazinecarboxylates, o-(2-imidazolin-2-yl)benzothiadiazinecarboxylates, o-(2-imidazolin-2-yl)benzoxathiazinecarboxylates, o-(2-imidazolin-2-yl)quinolinecarboxylates, o-(2-imidazolin-2-yl)dihydroquinolinecarboxylates, o-(2-imidazolin-2-yl)quinoxalinecarboxylates o-(2-imidazolin-2-yl)dihydroquinoxalinecarboxylates and the like.

There is a recognized need in agronomic practice for still more effective herbicidal agents and, especially, effective herbicidal agents which can be used in the presence of important agricultural crops without causing undue injury to said crops. Without adequate control, undesirable plant species can eliminate or reduce the yield of crops, reduce the quality and value of crops and reduce the efficient production and harvest of crops. The herbicidal imidazolinyl benzoheterocycles of the present invention exhibit effective control of a wide variety of undesirable monocotyledenous and dicotyledenous plant species and, moreover, demonstrate good selectivity towards important agronomic crops such as soybeans and wheat.

Herbicidally active imidazolinyl benzoheterocyclic compounds having the structure

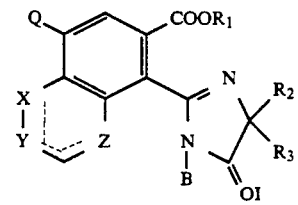
a.

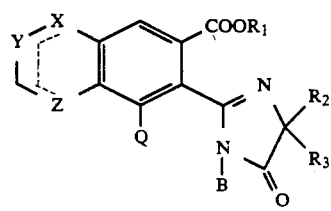
b.

wherein B is hydrogen and $R_1$, $R_2$, $R_3$, X, Y, Z and Q are as described hereinabove can be prepared from their imide nitrile precursors having the structure of formula I.

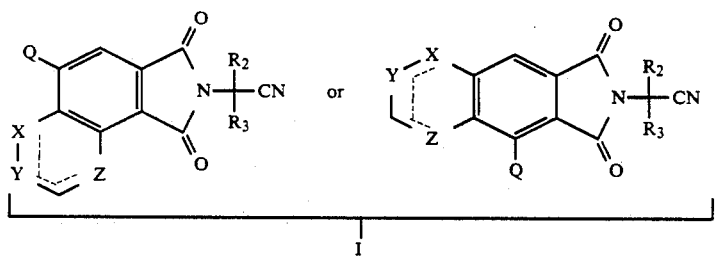

The nitrile groups on the formula I compounds can be hydrolyzed in the presence of sulfuric acid to give the corresponding amides and the resultant imide amides ring opened in the presence of an appropriate nucleophile such as an alkali metal alkoxide to give the ester diamide intermediates of formula II and their regioisomers. The formula II ester diamides can be converted to the desired compounds having structure a or b by reaction with phosphorous pentachloride in the presence of a solvent. In the case wherein $R_6$, $R_7$, $R_8$ or $R_9$ contain one or more hydroxy groups, these hydroxy groups are converted to chloro groups by this reaction. The reaction sequence is illustrated in flow diagram I.

FLOW DIAGRAM I

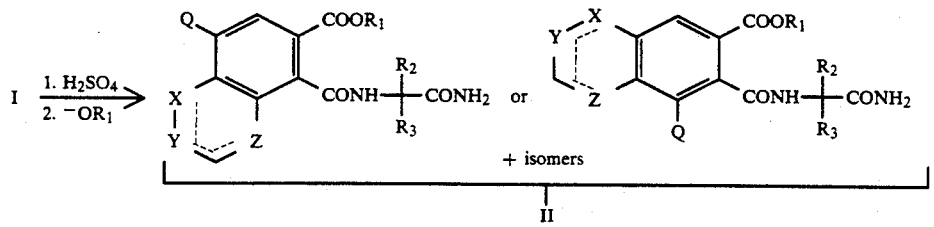

-continued
FLOW DIAGRAM I

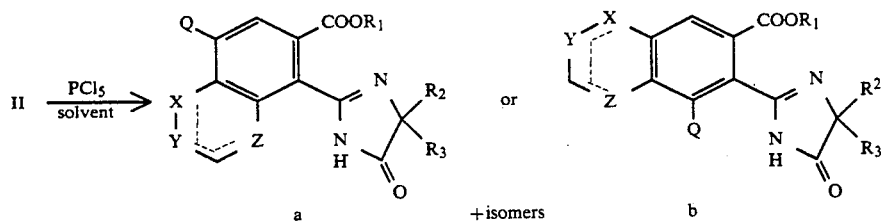

The regioisomers can be separated by standard chromatographic techniques such as reverse phase liquid chromatography.

Alternatively, compounds having structure a or b as described hereinabove and wherein $R_1$ is hydrogen can be prepared in 2 steps by reacting the appropriate phthalic anhydride with an amino amide of formula III in the presence of a base such as triethylamine, and optionally in the presence of a solvent, to obtain the corresponding acid diamide intermediates and their regioisomers and ring closing said intermediates in an aqueous alkali metal base followed by acidification to give the desired o-2(imidazolin-2-yl)benzoheterocyclic carboxylic acids having structure a or b and their regioisomers as shown in flow diagram II.

FLOW DIAGRAM II

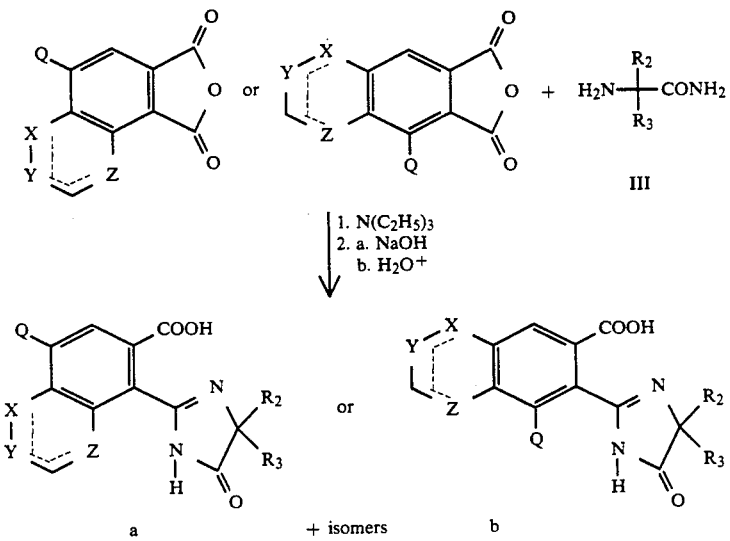

The regioisomers can be separated using standard chromatographic techniques such as reverse phase liquid chromatography.

Compounds having structure c and d can be prepared from the appropriate imide nitriles of formula I by the acid hydrolysis of the nitrile groups to give the corresponding imide amides and the cyclization thereof in the presence of an alkali metal hydride such as sodium hydride to give the desired indoloheterocyclic diones as shown in flow diagram III.

FLOW DIAGRAM III

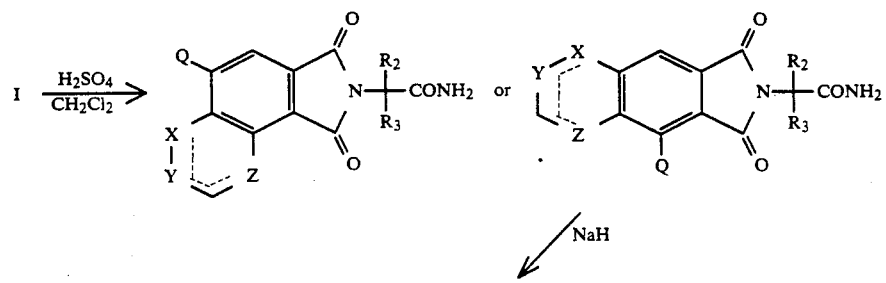

FLOW DIAGRAM III

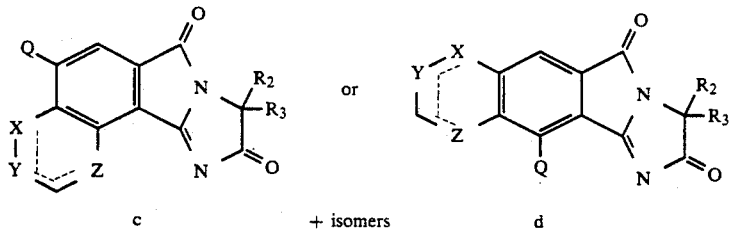

c  + isomers  d

Compounds having structure a and b wherein $R_1$ is other than hydrogen and B is hydrogen may be prepared from compounds having structure c or d by reacting said compounds with an appropriate nucleophile such as an alkali metal alkoxide as shown in flow diagram IV.

FLOW DIAGRAM IV

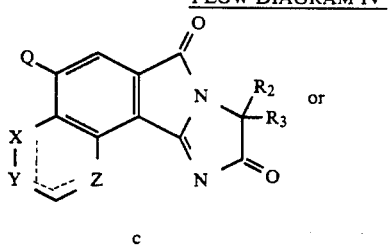

c

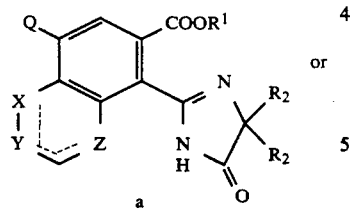

d

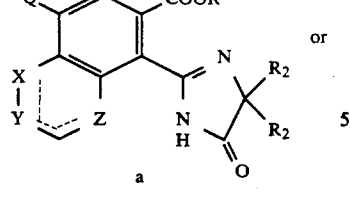

a

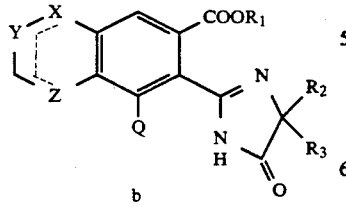

b

Compounds having structure e or f can be prepared by reacting the o-(2-imidazolin-2-yl)benzoheterocyclic carboxylic acids having structure a or b wherein B is hydrogen with dicyclohexylcarbodiimide (DCC) in the presence of a non-protic solvent as shown in flow diagram V.

FLOW DIAGRAM V

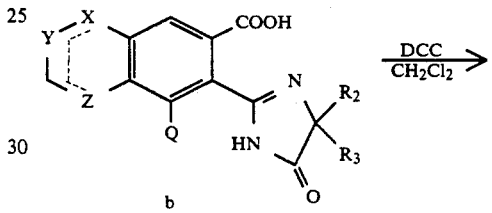

a

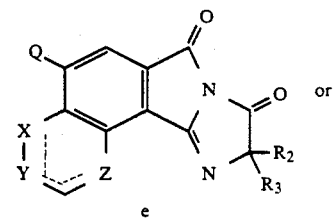

b

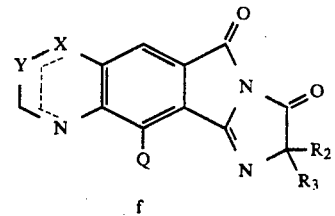

e

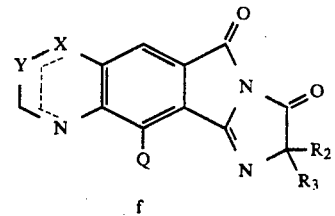

f

Compounds of the invention having structure b wherein Y is O, S or $NR_9$ and X and Z are $CH_2$ may be prepared using a cobalt catalyzed [2+2+2] cycloaddition reaction as described by K. P. C. Vollhardt in *Accounts of Chemical Research*, 1977, 10,1. The starting material is prepared by alkylating the appropriate butyne of formula IV with propargyl bromide to give the diacetylene of formula V. Said formula V diacetylene undergoes a [2+2+2] cycloaddition with dimethylacetylene dicarboxylate in the presence of cyclopentadienylcobaltcarbonyl catalyst and ultraviolet radiation to give the desired intermediate diester of formula VI. The diester can then be converted to the corresponding anhydride of formula VII using methods conventional in the art such as base hydrolysis followed by acidification and anhydride formation as shown in flow diagram VI.

FLOW DIAGRAM VI

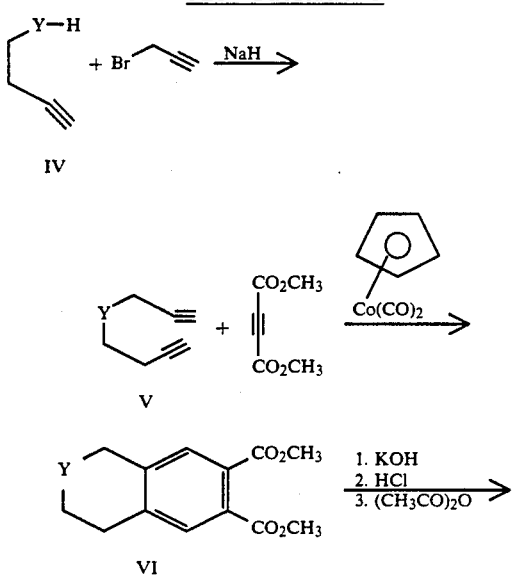

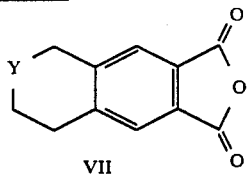

The formula VII anhydride is converted to compounds having structure b wherein Y is O, S or $NR_9$ and X and Z are $CH_2$ as shown in flow diagram II.

Compounds of the invention having structure a wherein Z is N and X and Y are CH may be prepared from 8-aminonaphthalenesulfonic acid. Using the procedure described by Schenkel-Rudin in *Helvetica Chimica Acta*, 1456, the 8-aminonaphthalenesulfonic acid is converted to the quinolinol of formula VIII. Treatment of the formula VIII compound with nitric acid followed by acetic anhydride affords the desired anhydride intermediate of formula IX. Said formula IX anhydride is then reacted with an aminonitrile of formula X to give the compound of formula I wherein Z is N and X and Y are CH. The formula I imide nitrile is then hydrolyzed to the corresponding imide amide and ring closed to give compounds having structure c as shown in flow diagram III or, alternatively, treated with aqueous base to give the compounds having structure a. The reaction sequence is illustrated in flow diagram VII.

FLOW DIAGRAM VII

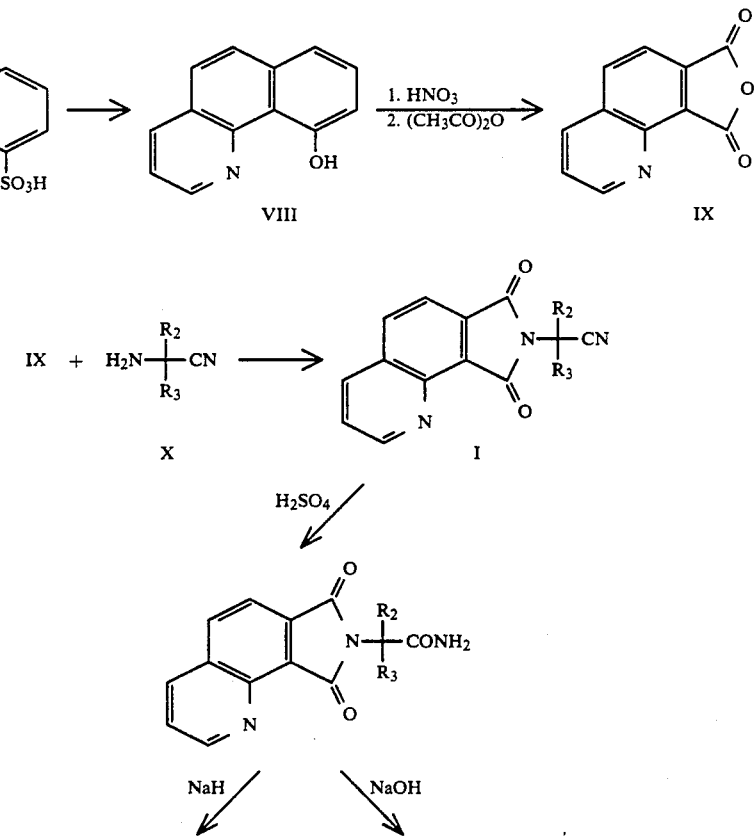

FLOW DIAGRAM VII -continued

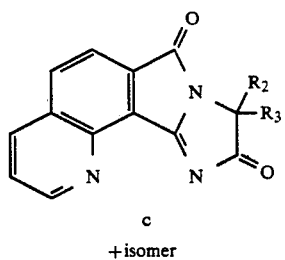

c
+isomer

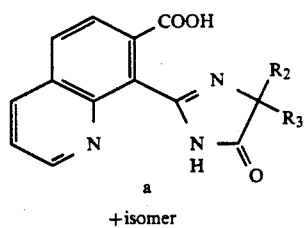

a
+isomer

Similarly, compounds having structure b wherein Z is N and X and Y are CH may be prepared from 3,4-dimethylaniline. Using the same procedure described in *Canadian Journal of Research*, 1942, 20B, 133, 3,4-dimethylaniline is converted to 6,7-dimethylquinoline which may then be oxidized using sodium dichromate and esterified to dialkyl 6,7-quinolinedicarboxylate. The thus-obtained diester may be converted to the corresponding anhydride using standard techniques such as base hydrolysis followed by acidification and anhydride formation. Said anhydride may then be converted to compounds having structure b wherein $R_1$ and B are hydrogen as shown in flow diagram II. The reaction sequence is illustrated in flow diagram VIII.

FLOW DIAGRAM VIII

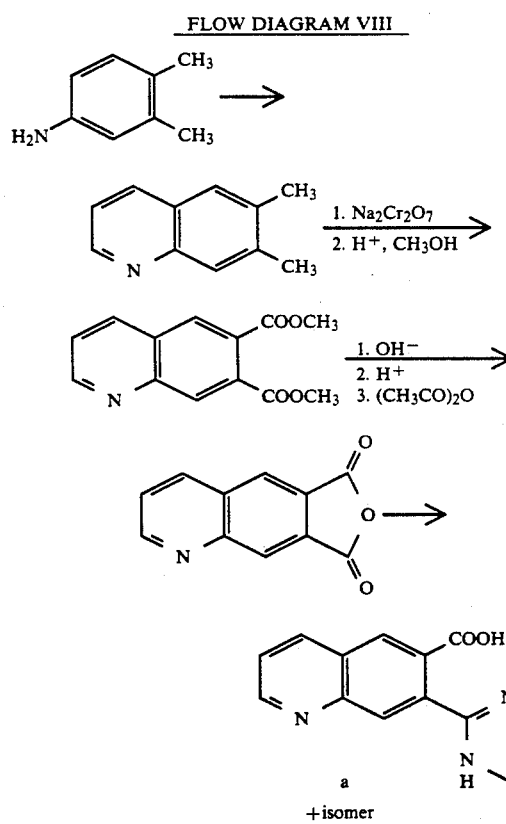

Compounds having structure b wherein X and Z are N and Y is CH may be prepared by the condensation of dimethyl 3,4-diaminophthalate with glyoxal to give the quinoxaline diester of formula XI, converting said formula XI diester to the corresponding anhydride using the above-described techniques and then forming the desired o-imidazolinylquinoxalinecarboxylate as shown in flow diagram II. The reaction sequence is illustrated in flow diagram IX.

FLOW DIAGRAM IX

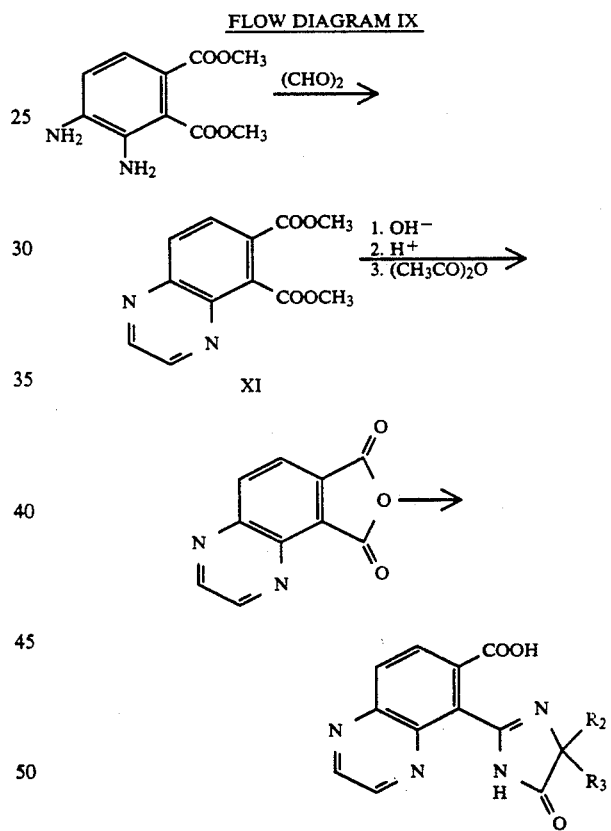

Of course, all of the compounds hereinabove described having structure a or b wherein $R_1$ and B are hydrogen may be converted to the corresponding indoloheterocyclic diones having structure c or d and structures e or f by repeating the procedures illustrated in flow diagrams III and V, respectively.

Compounds having structure a or b wherein $R_1$ is other than hydrogen or a cation and B is $COR_4$ or $SO_2R_5$ may be prepared by reacting compounds having structure a or b wherein $R_1$ is other than hydrogen or a cation and B is hydrogen with an acyl halide such as an acyl chloride or a sulfonyl halide such as a sulfonyl chloride to obtain the desired products wherein B is $COR_4$ or $SO_2R_5$. The reaction is shown in flow diagram X.

FLOW DIAGRAM X

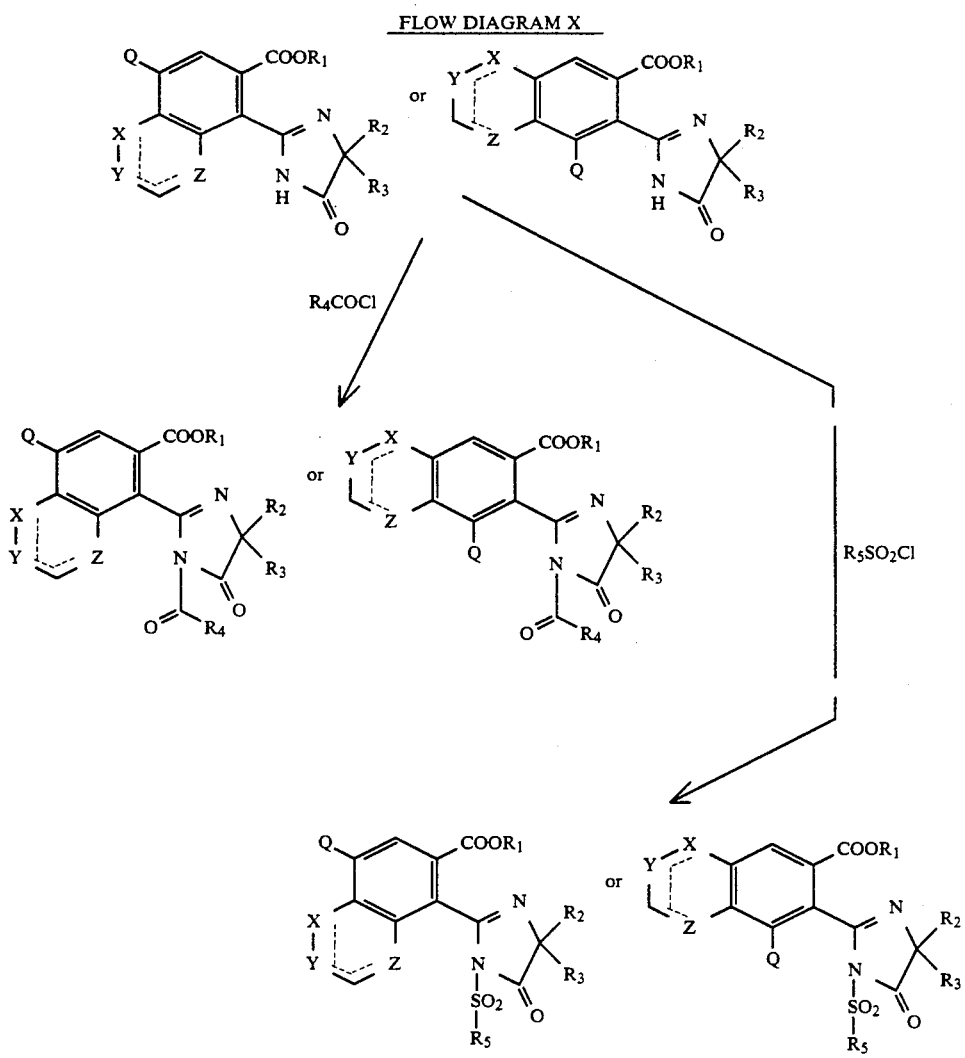

Alternatively, compounds having structure a or b wherein $R_1$ is other than hydrogen or a cation and B is $COR_4$ may be prepared by reacting compounds having structure a or b wherein $R_1$ is other than hydrogen or a cation and B is hydrogen with an acid anhydride of formula $(R_4CO)_2O$.

The imidazolinyl benzoheterocyclic compounds of the present invention are highly effective for controlling a variety of undesirable monocotyledenous plant species such as barnyardgrass, foxtail, purple, nutsedge, wild oats, quackgrass and the like and dicotyledenous plant species such as field bindweed, matricaria, morningglory, wild mustard, ragweed, velvetleaf and the like. Control of the above-said plant species can be achieved by applying the compounds of the invention to the foliage of said plants or to soil or water containing seeds or other propagating organs thereof at rates of about 0.016 to 4.0 kg/ha.

Surprisingly, it has been found that certain compounds of the invention are well tolerated by agronomic crops such as soybeans and wheat when said compounds are applied to the foliage of said crops or to soil containing the seeds or propagating organs thereof at rates of about 0.016 to 1.000 kg/ha.

Soybeans are an increasingly important worldwide source of high quality protein and are the most important edible legume produced today. Wheat is the second most important cereal crop in the United States and the leading cereal crop in both Canada and the United States.

The imidazolinyl benzoheterocyclic compounds may be applied as compositions comprising an inert solid or liquid diluent and a herbicidally effective amount of a compound of the invention. For example, they may be applied in the form of liquid sprays such as aqueous concentrates, emulsifiable concentrates and the like or as solid formulations such as wettable powders, dispersable granulars, granular formulations and the like.

When the herbicidally active compounds are water soluble, they may simply be dissolved in water and applied as an aqueous spray. Said compounds may also be formulated as emulsifiable concentrates and diluted with water just prior to spray application. A typical emulsifiable concentrate composition can be prepared by dissolving about 5% to 25% by weight of the active compound in about 65% to 90% by weight of N-methylpyrrolidone, isophorone, butyl cellosolve, methyl acetate or the like and dispersing therein about 5% to 10% by weight of a nonoionc surfactant such as an alkylphenoxy polyethoxy alcohol.

Wettable powder compositions can be prepared by grinding together about 20% to 45% by weight of a finely divided carrier such as kaolin, bentonite, diatomaceous earth, attapulgite or the like with about 40% to 80% by weight of the herbicidally active compound and about 2% to 5% by weight of a nonionic surfactant such as an alkyl phenoxy polyethoxy alcohol.

Typical granular products can be prepared by dissolving the active compound in a solvent such as methylene chloride, N-methylpyrrolidone or the like and spraying the resultant solution on a clay carrier such as attapulgite, or kaolin or the like in such a manner so as to produce about 3% to 20% by weight of the active compound and about 80% to 97% by weight of the carrier.

In order to facilitate a further understanding of the invention, the following examples are presented primarily for the purpose of illustrating certain more specific details thereof. The invention is not to be deemed limited thereby except as defined in the claims.

The term kg/ha designates kilograms per hectare. The terms $^{13}$CNMR, $^1$HNMR and IR designate carbon 13 and proton nuclear magnetic resonance and infrared, respectively. The term HPLC designates high pressure liquid chromatography. All parts are parts by weight, unless otherwise noted.

EXAMPLE 1

Preparation of 7,8-quinolinedicarboxylate anhydride

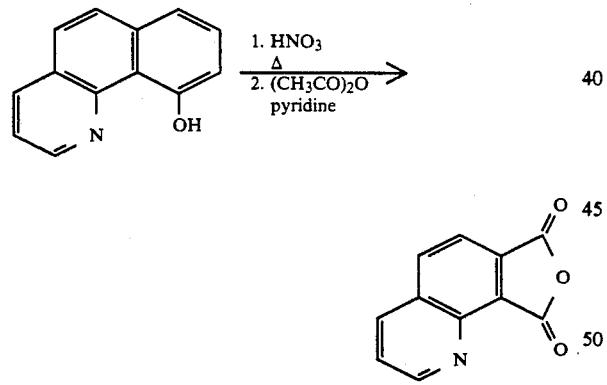

Nitric acid, (45 mL, 90%) is added slowly to benzo[h-]quinolin-10-ol (5.30 g, 27.2 mmol) in an ice bath; the reaction temperature is slowly raised to 80° C. over a 2 hour period and held at 80° C. for 0.5 hours, then brought to room temperature. The reaction mixture is diluted slowly with water and concentrated in vacuo. to give a dark residue which is taken up in tetrahydrofuran (50 mL), acetic anhydride (30 mL) and pyridine (10 mL), resulting in an exotherm. After the exotherm has ceased, the mixture is concentrated in vacuo, and reconcentrated after dilution with xylenes, affording the title product as a dark gum (7.00 g), identified by mass spectrometric analysis.

EXAMPLE 2

Preparation of 1,3-Dihydro-α-isopropyl-α-methyl-1,3-dioxo-2H-pyrrolo[3,4-h]quinoline-2-acetamide

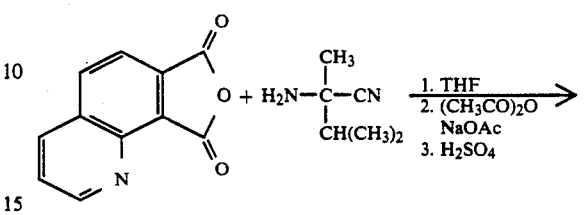

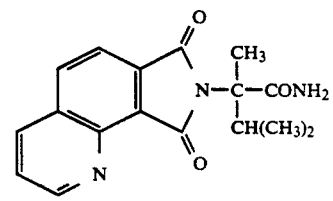

To a suspension of 7,8-quinolinedicarboxylic anhydride (28.0 g, 0.140 mol) in tetrahydrofuran is added α-methylvalinonitrile (12.0 g, 0.107 mol). After 15 minutes, acetic anhydride is added and the mixture is heated on a steam bath. The reaction mixture is cooled, treated with sodium acetate (3.00 g, 0.036 mol), stirred for 3 hours at reflux temperature, allowed to stand overnight at room temperature and concentrated in vacuo to give a black residue. The residue is taken up in methylene chloride and water and filtered through diatomaceous earth. The filtrate is separated and the aqueous layer is extracted with methylene chloride. The combined organic layers are washed with saturated sodium bicarbonate, dried (Na$_2$SO$_4$) and concentrated in vacuo to a give black gum. Flash chromatography (silica gel, ethyl acetate:hexanes eluent) of this gum affords the crude imide nitrile intermediate as a tan gum. The material is treated with concentrated sulfuric acid for 1 hour at room temperature, diluted with ice water and extracted with methylene chloride. The organic extract is dried and concentrated in vacuo to afford a tan solid. Recrystallization from chloroform:hexanes yields the title product as a light tan solid, 3.50 g, mp 215°–217° C.

EXAMPLE 3

Preparation of Methyl 8-(4-isopropyl-4-methyl-5-oxo-2-imidazolin-2-yl)-7-quinolinecarboxylate (I) and methyl 7-(4-isopropyl-4-methyl-5-oxo-2-imidazolin-2-yl-8-quinolinecarboxylate (II)

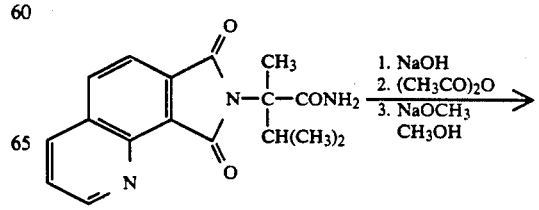

-continued

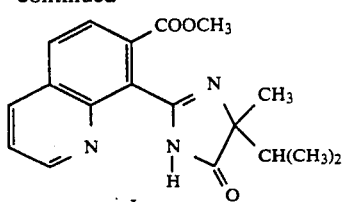

+

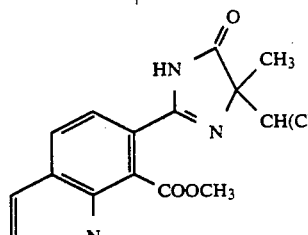

A mixture of 3-dihydro-α-isopropyl-α-methyl-1,3-dioxo-2H-pyrrolo[3,4-h]quinoline acetamide (2.85 g, 9.16 mmol) and 5N sodium hydroxide (10.0 mL, 50.0 mmol) is stirred 4 hours at 100° C., cooled to room temperature, diluted with water and acidified to pH 4 with 6N sulfuric acid. The reaction mixture is extracted with methylene chloride, the organic layer is separated, dried and concentrated in vacuo to afford a brown gum. The aqueous phase affords additional material upon concentration in vacuo. The residues are combined, taken up in acetic anhydride (10 mL) and pyridine (15 mL), and heated for 5 minutes on a steambath. The solvents are removed in vacuo; the residue is taken up in methanol, treated with powdered sodium methoxide to pH 10-12, stirred overnight and neutralized to pH 7-8 with acetic acid. After removal of the methanol in vacuo, the residue is flash chromatographed (silica gel, gradient elution ether:hexanes to ether) to afford the title products (I) as a white solid (0.870 g, 29.2%), mp 184°-189° C., and (II) as a tan solid (0.800 g, 26.8%), mp 190°-197° C.

EXAMPLE 4

Preparation of 8-(4-Isopropyl-4-methyl-5-oxo-2-imidazolin-2-yl)-7-quinolinedicarboxylic acid

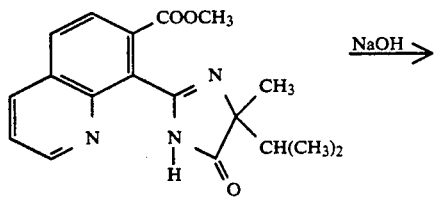

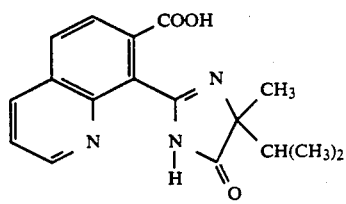

A mixture of methyl 8-(4-isopropyl-4-methyl-5-oxo-2-imidazolin-2-yl)-7-quinolinecarboxylate (0.500 g, 1.54 mmol) and 2N sodium hydroxide (2.00 mL, 4.00 mmol) is heated to 70° C., cooled to 50° C., stirred for 20 minutes, cooled to room temperature, acidified to pH 4 with concentrated sulfuric acid and filtered. The filter cake is recrystallized from methylene chloride to afford the title product as a white solid (0.250 g, 52.1%), mp 200°-201° C.

EXAMPLE 5

Preparation of Dimethyl-6,7-quinolinedicarboxylate

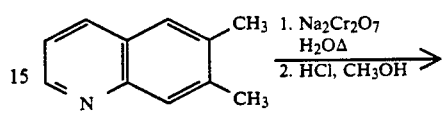

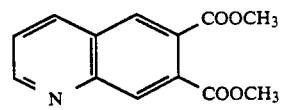

A mixture of 6,7-dimethylquinoline (11.2 g, 0.0714 mol), sodium dichromate (57.4 g, 0.193 mol) and water is heated in an autoclave. After 1 hour, the bath temperature is 250° C. and the pressure is 520 psi; the mixture is held at this temperature and pressure for 3.75 hours, stirred for 3 days at room temperature and filtered. The filtrate is washed with methylene chloride and concentrated in vacuo to give a yellow solid. The solid is slurried in toluene, filtered, dried, taken up in methanol, cooled to −20° C., bubbled through with hydrogen chloride for 20 minutes, stirred overnight at room temperature, and filtered. The filtrate is concentrated to a volume of 400 mL, poured onto ice, neutralized with solid sodium bicarbonate and extracted with methylene chloride. The organic extract is dried (NaSO₄) and concentrated in vacuo to a red-dish-brown oil. Flash chromatography (silica gel, 50% hexane:ethyl acetate eluent) affords the title product as a yellow solid (6.44 g, 36.8%). Recrystallization gives mp 101°-102° C.

EXAMPLE 6

Preparation of 6,7-Quinolinedicarboxylic anhydride

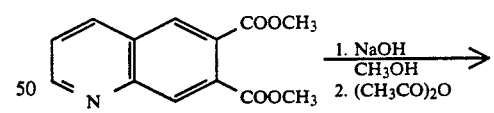

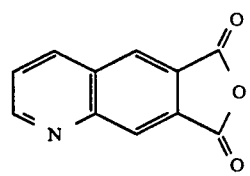

A mixture of dimethyl 6,7-quinolinedicarboxylate (3.00 g, 12.2 mmol), methanol and 10% aqueous sodium hydroxide (25 mL, 62.5 mmol) is stirred overnight at room temperature, cooled, acidified to pH 4-5 with concentrated sulfuric acid, diluted with acetone and filtered. The filtrate is concentrated in vacuo to give a tan solid, which is suspended in acetic anhydride (100 mL), stirred overnight at 56° C. and cooled. The solvent is removed in vacuo to afford the title product as a tan

EXAMPLE 7

Preparation of
2-Isopropyl-2-methyl-3H-imidazo[1',2':1,2]pyrrolo[4,3
g]quinoline-3(2H),5-dione and
2-isopropyl-2-methyl-3H-imidazo[1',1':5,1]pyrrolo-[4,3-g]quinoline-3(2H),5 dione

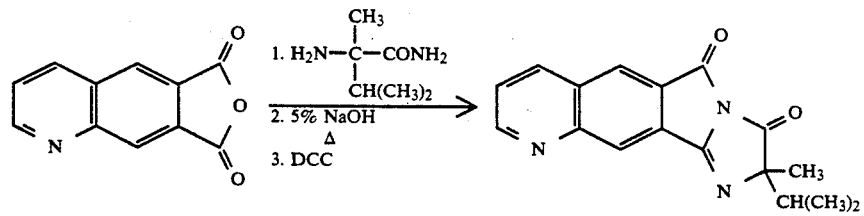

A suspension of 6,7-quinolinedicarboxylic anhydride (1.20 g, 4.88 mmol) in acetonitrile at 0° C. is treated with α-methylvalinamide (0.860 g, 6.61 mmol), stirred overnight at ambient temperature, diluted with methylene chloride, stirred 4 hours at room temperature, and concentrated in vacuo to give a tan solid. The solid is taken up in 5% sodium hydroxide (200 mL, 125 mmol) washed with methylene cloride, stirred for 1.5 hours at 60°-65° C. and at room temperature for 3 days, cooled in an ice bath, acidified to pH 1 with concentrated hydrochloric acid and concentrated in vacuo to afford a residue. The residue is slurried in methanol, filtered and and the filtrate is concentrated in vacuo to give a tan solid. This solid is chromatographed through a column of silica gel with 20% methanol:methylene chloride, then slurried in hot methanol, and filtered hot to remove inorganic impurities. The methanolic filtrate is concentrated in vacuo to give an off-white solid.

The solid is suspended in methylene chloride, treated with dicyclohexylcarbodiimide (2.90 g, 14.1 mmol), stirred for 5 days at room temperature, and filtered. The filtrate is concentrated in vacuo to a yellow semisolid which is chromatographed (silica gel, 1% methanol:methylene chloride eluent) to afford a white solid. The solid is slurried in methylene chloride, filtered and the filtrate is concentrated in vacuo to afford the title product as a white solid (1.10 g, 76.9%), identified by mass spectral analysis.

EXAMPLE 8

Preparation of Methyl
7-(4-isopropyl-4-methyl-5-oxo-2-imidazolin-2-yl)-6-quinolinecarboxylate and methyl
6-(4-isopropyl-4-methyl-5-oxo-2-imidazolin-2-yl)-7-quinolinecarboxylate 1:1 mixture)

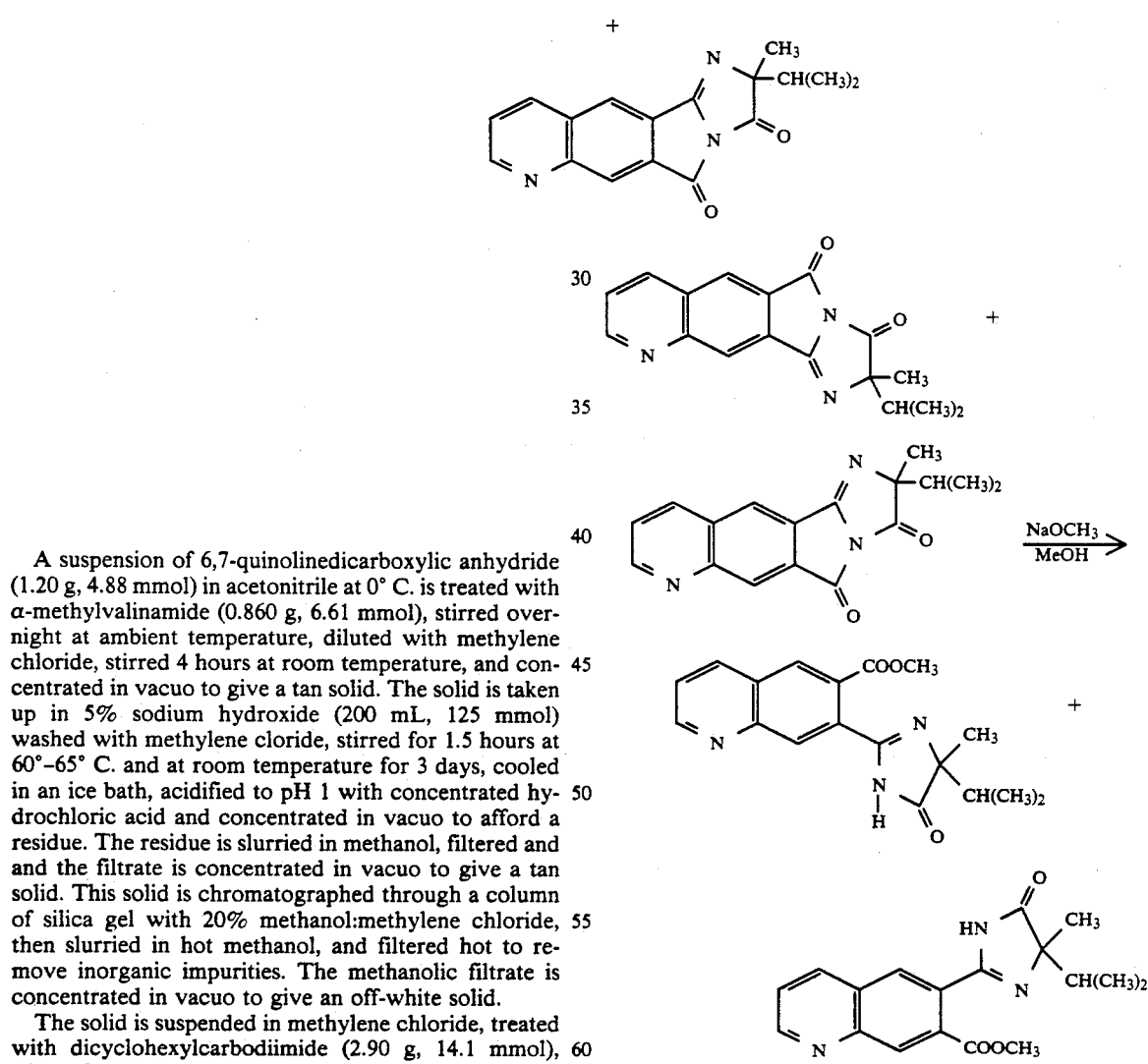

A mixture of 2-isopropyl-2-methyl-3H-imidazo[1',2':1,2](and [2',1':5,1])pyrrolo[4,3-g]quinoline-3(2H), 5-diones (1.10 g, 3.76 mmol) is added to a solution of sodium methoxide (0.100 g, 1.85 mmol) in methanol under a nitrogen atmosphere, stirred overnight at room temperature, treated with glacial acetic acid to pH 6 and concentrated in vacuo to give a pale-

EXAMPLE 9

Preparation of 3-Butylnyl-2-propynyl ether

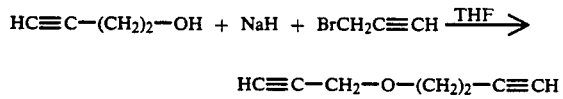

A suspension of sodium hydride (6.63 g, 0.166 mol, 60% oil dispersion) in tetrahydrofuran is cooled to −18° C. under nitrogen atmosphere, treated dropwise with a solution of 3-butyn-1-ol (11.3 g, 0.161 mol) in tetrahydrofuran, stirred for 30 minutes at −18° C. to 0° C., treated dropwise with a solution of propargyl bromide (60.0 g, 0.400 mol) in tetrahydrofuran, stirred for 22 hours at ambient temperature, poured into ice water and extracted with ether. The organic phase is dried (MgSO₄) and concentrated in vacuo to afford a brown liquid residue. The residue is distilled to give the title product as a colorless liquid (9.06 g, 52.1%), bp 79°–82°/85 torr.

EXAMPLE 10

Preparation of Dimethyl 3,4-dihydro-1H-2-benzopyran-6,7-dicarboxylate

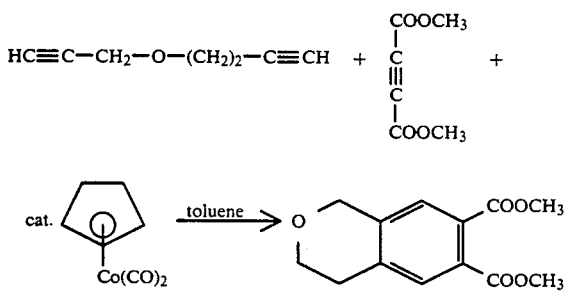

A mixture of 3-butynyl-2-propynyl ether (37.2 g, 0.344 mol), dimethylacetylenedicarboxylate (48.9 g, 0.344 mol) and toluene is divided into 2 portions and transferred to 2 addition funnels connected to the reaction vessel. The apparatus is fitted with a condenser and evacuated 4 times with a Firestone valve and nitrogen. The cobalt catalyst is added in equal amounts to each addition funnel. The reaction vessel which contains approximately 2L toluene is heated to 105° C. under a nitrogen atmosphere with stirring. The contents of the addition funnels are added dropwise at equivalent rates, at 105° C., over a 4 hour period. The reaction mixture is stirred overnight at 100° C. under a heat lamp (Visible light), cooled to room temperature and filtered through diatomaceous earth. The filtrate is concentrated in vacuo to a brown oil, which is flash chromatographed (silica gel, 95% hexane:ether acetate eluent) to afford the title product as a pale orange solid (16.5 g, 19.2%) identified by NMR analysis.

yellow solid. The solid is taken up in methylene chloride and washed with water, dried (NaSO₄) and concentrated in vacuo to afford an off-white solid. This crude material is chromatographed (silica gel, 50% methylene chloride:ethyl acetate as eluent) to yield the title products as a 1:1 mixture (white solid) (0.390 g, 32 0%), mp 174°–178° C.

EXAMPLE 11

Preparation of Dipotassium 3,4-dihydro-1H-2-benzopyran-6,7-dicarboxylate

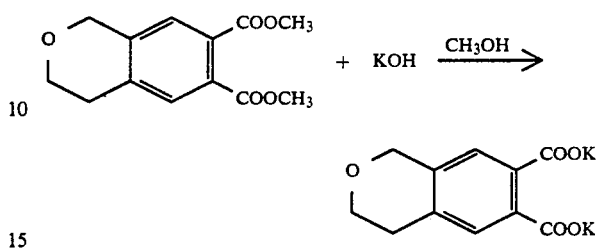

A mixture of dimethyl 3,4-dihydro-1H-2-benzopyran-6,7-dicarboxylate (16.5 g, 0.0659 mol), potassium hydroxide (10.4 g, 0.184 mol) and methanol is stirred for 3 hours at 49° C., cooled to room temperature, and filtered. The filter cake is dried to afford the title product as a cream-colored solid (14.5 g) mp >250° C.

EXAMPLE 12

Preparation of 3,4-dihydro-1H-2-benzopyran-6,7-dicarboxylic acid

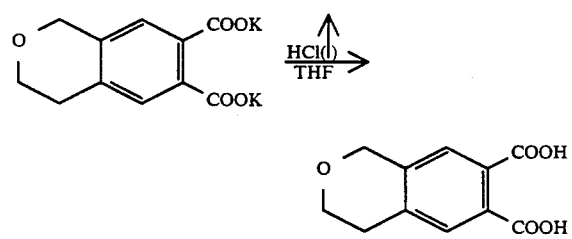

A suspension of the dipotassium salt of the title product (14.2 g, 47.6 mmol) in tetrahydrofuran is cooled to 5° C., bubbled through with hydrogen chloride gas for 3 minutes (exotherm 5° C.–30° C.) and stirred for 2 hours at ambient temperatures. The potassium chloride is removed by filtration. The filtrate is concentrated in vacuo to give a pale yellow solid which is heated in ether on a steam bath, cooled, and filtered to give the title product as a white solid (7.50 g, 70.8%), mp 179°–181° C.

EXAMPLE 13

Preparation of 3,4-Dihydro-1H-2-benzopyran-6,7-dicarboxylic anhydride

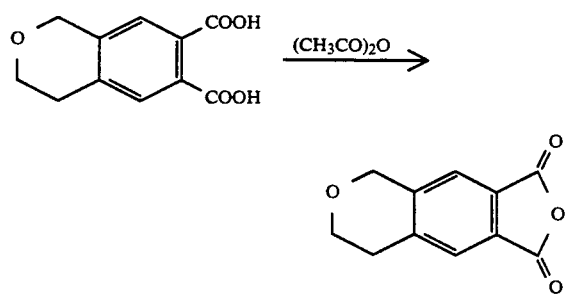

A mixture of 3,4-dihydro-1H-2-benzopyran-6,7-dicarboxylic acid (7.28 g, 32.8 mmol) and acetic anhydride is stirred for 3.5 hours at 100° C., allowed to stand overnight at room temperature and filtered. The filter cake is washed with ether and dried to give the title product as a white solid (5.53 g, 82.7%). Recrystallization gives mp 156°-158° C.

EXAMPLE 14

Preparation of 7-[(1-Carbamoyl-1,2-dimethylpropyl)-carbamoyl]-3,4-dihydro-1H-2-benzopyran 6-carboxylic acid and 6-[(1-carbamoyl-1,2-dimethylpropyl)carbamoyl]-3,4-dihydro-1H-2-benzopyran-7-carboxylic acid (1:1 mixture)

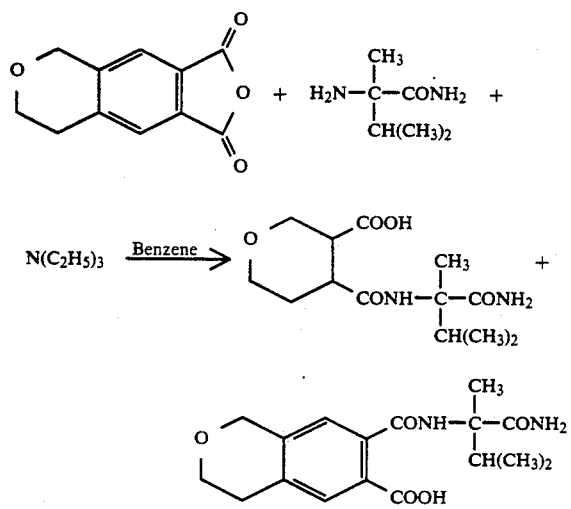

A mixture of 3,4-dihydro-1H-2-benzopyran-6,7-dicarboxylic anhydride (5.50 g, 26.9 mmol) and α-methylvalinamide (3.28 g, 29.3 mmol) in benzene is stirred for 2 hours at 64° C. and 0.5 hours at 80° C., treated with triethylamine (3.70 mL, 26.6 mmol), stirred overnight at 80° C., cooled to room temperature and filtered. The filter cake is dried to give the title product mixture as a white solid (9.72 g, 100%), mp 65°-80° C., identified by $^1$H and $^{13}$CNMR spectral analyses.

EXAMPLE 15

Preparation of 3,4-Dihydro-7-(4-isopropyl-4-methyl-5-oxo-2-imidazolin-2-yl)-1H-2-benzopyran-6-carboxylic acid and 3,4-dihydro-6-(4-isopropyl-4-methyl-5-oxo-2-imidazolin-2-yl)-1H-2-benzopyran-7-carboxylic acid (1:1 mixture)

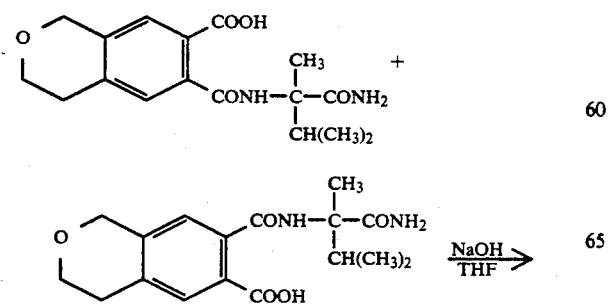

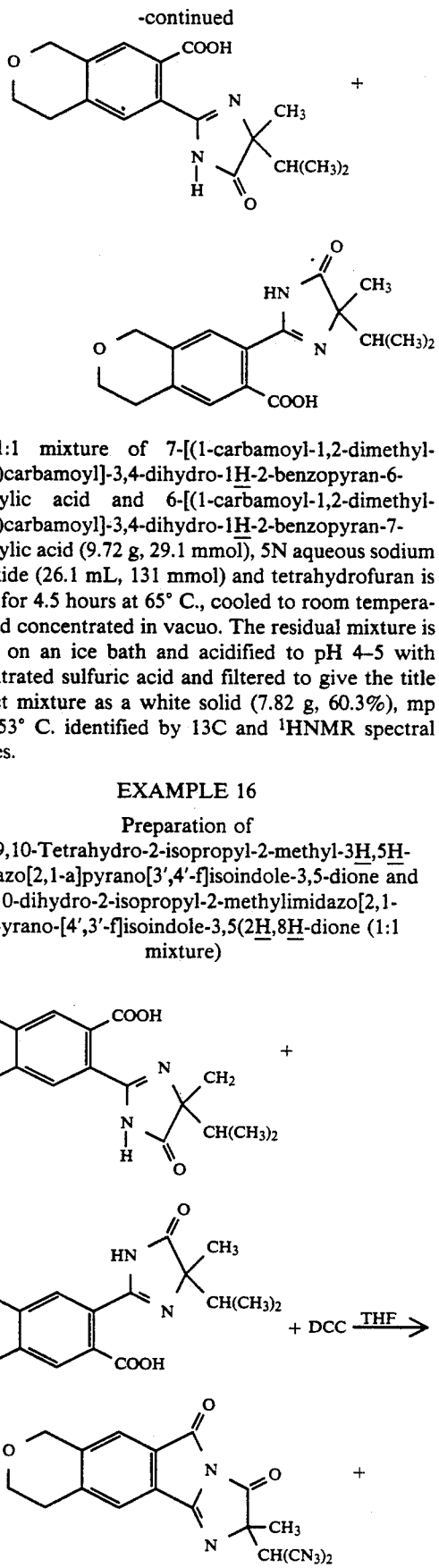

A 1:1 mixture of 7-[(1-carbamoyl-1,2-dimethylpropyl)carbamoyl]-3,4-dihydro-1H-2-benzopyran-6-carboxylic acid and 6-[(1-carbamoyl-1,2-dimethylpropyl)carbamoyl]-3,4-dihydro-1H-2-benzopyran-7-carboxylic acid (9.72 g, 29.1 mmol), 5N aqueous sodium hydroxide (26.1 mL, 131 mmol) and tetrahydrofuran is stirred for 4.5 hours at 65° C., cooled to room temperature and concentrated in vacuo. The residual mixture is cooled on an ice bath and acidified to pH 4-5 with concentrated sulfuric acid and filtered to give the title product mixture as a white solid (7.82 g, 60.3%), mp 137°-153° C. identified by 13C and $^1$HNMR spectral analyses.

EXAMPLE 16

Preparation of 2,7,9,10-Tetrahydro-2-isopropyl-2-methyl-3H,5H-imidazo[2,1-a]pyrano[3',4'-f]isoindole-3,5-dione and 7,10-dihydro-2-isopropyl-2-methylimidazo[2,1-a]pyrano-[4',3'-f]isoindole-3,5(2H,8H)-dione (1:1 mixture)

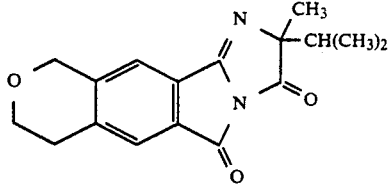

A solution of dicyclohexylcarbodiimide (6.1 g, 29.5 mmol) in tetrahydrofuran is added dropwise to a solution of a 1:1 mixture of 3,4-dihydro-7-(4-isopropyl-4-methyl-5-oxo-2-imidazolin-2-yl)-1H-2-benzopyran-6-carboxylic acid and 3,4-dihydro-6-(4-isopropyl-4-methyl-5-oxo-2-imidazolin-2-yl)-1H-2-benzopyran-7-carboxylic acid (5.00 g, 15.8 mmol) in tetrahydrofuran at 0° C. The reaction mixture is stirred overnight at ambient temperature and filtered. The filtrate is concentrated in vacuo to give a white solid residue which is chromatographed (silica gel, 95% methylene chloride:ethyl acetate eluent) to afford the title product mixture as a white solid, mp 142°–160° C.

EXAMPLE 17

Preparation of 7,10-Dihydro-3-isopropyl-3-methylidazo[2,1-a]pyrano[4',3'-f]isoindole-2,5(3H,8H)dione (I) and 9,10-dihydro-3-isopropyl-3-methyl-3H,5H-imidazo-[2,1-a]pyrano-[3',4'-f]isoindole-2,5(7H)dione (II)

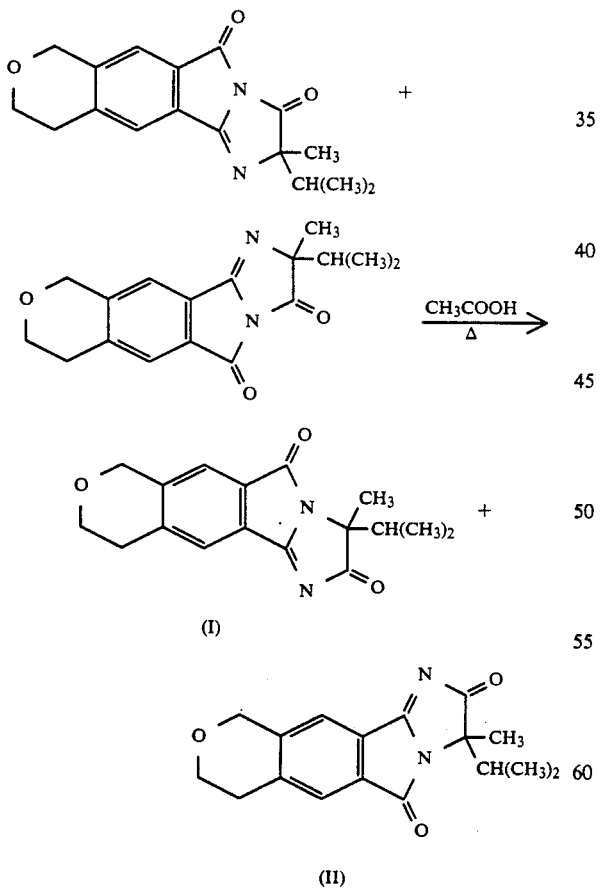

A solution of a 1:1 mixture of 2,7,9,10-tetrahydro-2-isopropyl-2-methyl-3H,5H-imidazo[2,1-a]pyrano[3',4'-f]isoindole-3,5-dione and 7,10-dihydro-2-isopropyl-2-methyl-imidazo[2,1-a]pyrano-[4',3'-f]-isoindole-3,5(2H,8H)-dione (1.00 g, 3.35 mmol) in glacial acetic acid (10 mL) is stirred for 22 hours at 98° C., cooled to room temperature and concentrated in vacuo to give a pale yellow wax residue. The residue is flash chromatographed (silica gel, methylene chloride:ethyl acetate) to afford three fractions of approximately equal $R_f$. In order of elution, the fractions are:

1. title compound (I), an off-white, solid, mp 174°–178° C.;
2. a 1:1 mixture of title compounds (I) and (II) mp 158°–165° C.;
3. title compound II, an off-white solid, mp 155°–158° C.

The fractions are identified by $^1H$ and $^{13}CNMR$ analyses.

EXAMPLE 18

Preparation of Methyl 3,4-dihydro-7-(4-isopropyl-4-methyl-5-oxo-2-imidazolin-2 yl)-1H-2-benzopyran-6-carboxylate (I) and methyl 3,4-dihydro-6-(4-isopropyl-4-methyl-5-oxo-2-imidazolin-2 yl)-1H-2-benzopyran-7-carboxylate (II) (1:1 mixture)

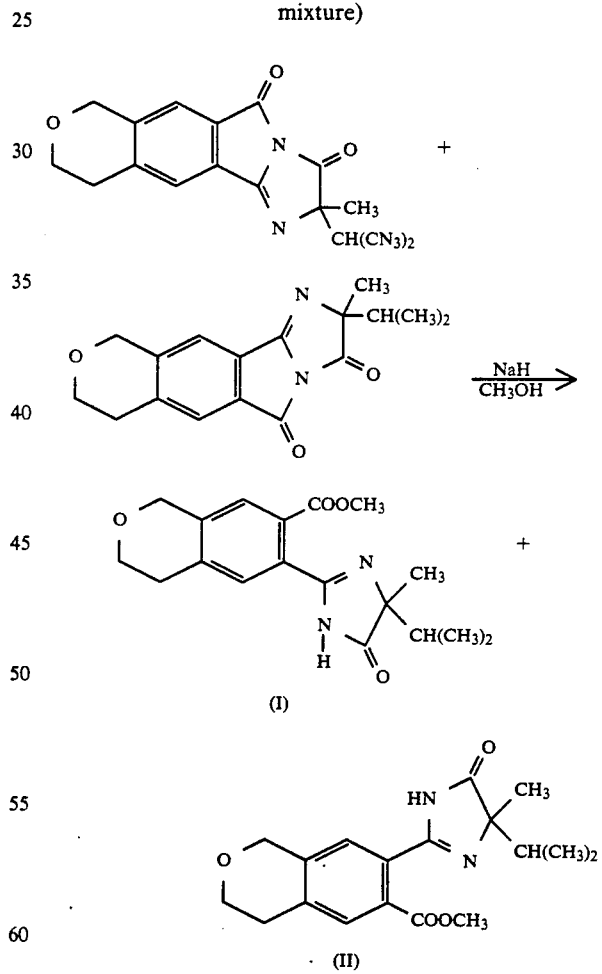

A catalytic amount of sodium hydride (60% oil dispersion) is added to a solution of a 1:1 mixture of 2,7,9,10-tetrahydro-2-isopropyl-2-methyl-3H,5H-imidazo[2,1-a]pyrano[3',4'-f]isoindole-3,5-dione and 7,10-dihydro-2-isopropyl-2-methyl-imidazo[2,1-a]pyrano[4',3'-f]isoindole-3,5(2H,8H)dione (2.03 g, 6.80 mmol) in methanol to pH 10. The reaction mixture is stirred for 21 hours at room temperature, treated with acetic acid to pH 6, and concentrated in vacuo to give an off-white solid residue. The residue is flash chromatographed (silica gel, 2% methanol:methylene chloride eluent) to afford a white solid which is purified by recrystallization from cyclohexane and flash chromatography (silica gel, 60% ethyl acetate:ether) to yield the title product as white crystals, mp 145°-149° C., identified by NMR spectral analysis.

EXAMPLE 19

Preparation of Dimethyl 5,6-quinolinedicarboxylate

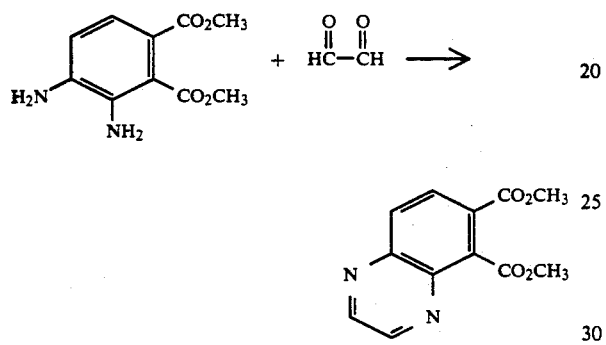

A mixture of dimethyl 3,4-diaminophthalate (11.2 g, 0.05 mol) in tetrahydrofuran is treated with glyoxal (2.9 g, 0.05 mol) in water at reflux temperature, stirred for 4 hours at reflux temperature and overnight at room temperature, and concentrated in vacuo. The resultant residue is partitioned between water and methylene chloride. The organic phase is dried (MgSO₄) and concentrated in vacuo to give a brown solid residue. Recrystallization from methanol gives the title product as a pink powder (9.67 g, 78.6%) mp 124°-125° C., identified by H¹NMR, C¹³NMR, and IR spectral analyses.

EXAMPLE 20

Preparation of 5.6-Quinolinedicarboxylic acid

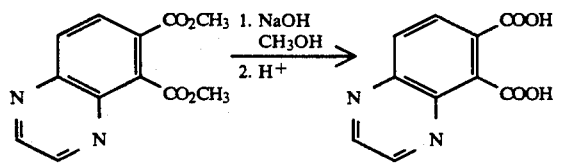

A mixture of dimethyl 5,6-quinolinedicarboxylate (2.46 g, 10.0 mmol), aqueous sodium hydroxide (5.0 mL, 5m, 25.0 mmol) and methanol is heated to 80° C., treated with water at 80° C. until the mixture is homogeneous, stirred for 2 hours at reflux temperature, cooled to 0° C., acidified to pH 4 with concentrated hydrochloric acid and filtered. The filter cake is air dried to give the title product as a white powder 2.00 g, 91.7%) mp >360 C, identified by H¹NMR spectroscopy.

EXAMPLE 21

Preparation of 5,6-Quinolinedicarboxylic anhydride

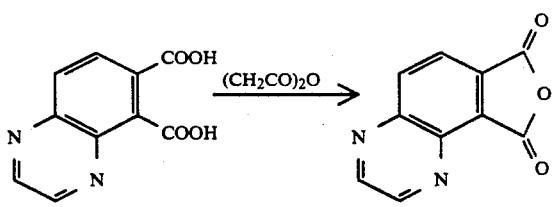

A mixture of 5,6-quinolinedicarboxylic acid and acetic anhydride is stirred for 2 hours at reflux temperature, cooled to 0° C. and filtered. The filter cake is dried to give the title product as yellow needles (1.50 g, 82.4%) mp 247°-50° C., identified by H¹NMR spectroscopy.

EXAMPLE 22

Preparation of 5-[1-Carbamoyl-1,2-dimethylpropyl)-carbamoyl]-6-quinolinedicarboxylic acid

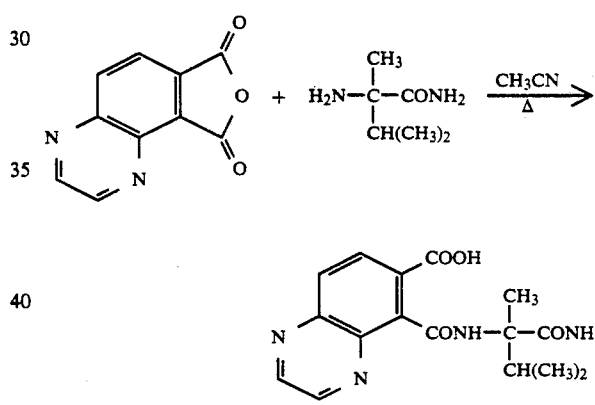

A mixture of 5,6-quinolinedicarboxylic anhydride (1.50 g, 7.49 mmol), α-methylvalinamide (1.02 g, 7.83 mmol) and acetonitrile is stirred for 3 hours at reflux temperature, cooled to 0° C. and filtered to afford the title product as a white powder (2.32 g, 93.9%), mp 203°-210° C., identified by H¹NMR, C¹³NMR and IR spectral analyses.

EXAMPLE 23

Preparation of 5-(4-Isopropyl-4-methyl-5-oxo-2-imidazolin-2-yl)-6-quinolinedicarboxylic acid

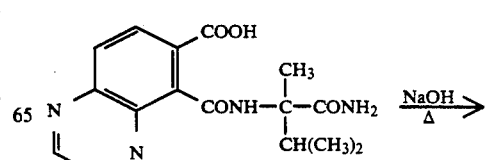

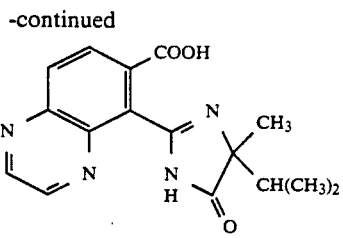

A mixture of 5-[(1-Carbamoyl-1,2-dimethylpropyl)-carbamoyl]-6-quinoxalinecarboxylic acid (1.30 g, 3.94 mmol), aqueous sodium hydroxide (1.38 mL, 10M, 13.8 mmol) and water is stirred for 3 hours at reflux temperature, cooled to 0° C., acidified to pH 4 with concentrated hydrochloric acid and filtered. The filter cake is recrystallized from methanol-acetonitrile to afford the title product as a white powder, (1.00 g, 81.3%), mp 211°–214° C., identified by IR, $N^1$NMR, $C^{13}$NMR, $^1$H coupled $C^{13}$NMR and mass spectral analyses.

EXAMPLE 24

Preemergence Herbicidal Evaluation of Test Compounds

The preemergence herbicidal activity of the imidazolinyl benzoheterocyclic compounds of the present invention is demonstrated by the following tests in which the seeds of a variety of monocotyledenous and dicotyledenous plant species are individually mixed with potting soil and planted on top of approximately one inch of soil in one pint cups. After planting, the cups are sprayed with an aqueous acetone solution containing the test compound. Said test solution consists of a 50/50 acetone/water mixture and a test compound in sufficient quantity to provide the equivalent of about 0.016 kg/ha to 4.0 kg/ha of active compound when applied to the soil through a spray nozzle operating at 40 psi for a predetermined time. The treated cups are then placed on greenhouse benches and cared for in accordance with conventional greenhouse procedures.

From 4 to 5 weeks after treatment, the test cups are evaluated and rated according to the rating system set forth below. The results of herbicide evaluations are expressed on a rating scale of 0–9. The scale is based upon a visual observation of plant stand, vigor, malformation, size, chlorosis and overall plant appearance as compared with a control.

The data obtained are recorded in Table I. Where more than one test is performed for a given compound, the average rating is shown.

HERBICIDE RATING SCALE

| Rating | Meaning | % Control (Compared To Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

PLANT SPECIES USED

| Header Abb | Common Name | Scientific Name |
|---|---|---|
| Barnyardgr | Barnyardgrass | Echinochloa crus-galli, (L) Beau |
| Foxtail Sp | Foxtail Spp. | Setaria Spp. |
| P Nutsedge | Nutsedge, Purple | Cyperus rotundus, L. |
| Wild Oats | Oat, Wild | Avena fatua, L. |
| Quackgrass | Quackgrass | Agropyron repens, (L) Beauv. |
| Fld Bindwd | Bindweed, Field (Rhizome) | Convolvulus arvensis, L. |
| Mrnglry Sp | Morningglory Spp. | Ipomoea Spp. |
| Wild Mustd | Mustard, Wild | Brassica kaber, (DC) L.C.Wheelr |
| Velvetleaf | Velvetleaf | Abutilon theophrasti, Medic. |
| Wht Fenman | Wheat, Fenman | Triticum aestivum, Fenman |
| Soybean Br | Soybean, Bragg | Glycine, max (L) Men. CV Bragg |

TABLE I

| Compound Name | Rate Kg/ha | Barny ardgr | Foxta il Sp | P Nut sedge | Wild Oats | Quack grass | Fld Bl ndwd | Mrngl ry Sp | Wild Mustd | Velve tleaf | Wht F enman | Soybe an Br |
|---|---|---|---|---|---|---|---|---|---|---|---|---|
| 8-(4-Isopropyl-4-methyl-5-oxo-2-imidazolin-2-yl)-7-quinolinecarboxylic acid | .500 | 9 | 0 | 8 | 0 | 4 | 9 | 8 | 9 | 6 | 2 | 2 |
|  | .250 | 4 | 0 | 8 | 0 | 1 | 9 | 6 | 8 | 4 | 1 | 1 |
|  | .125 | 2 | 0 | 6 | 0 | 0 | 9 | 3 | 7 | 4 | 0 | 3 |
| Methyl 8-(4-isopropyl-4-methyl-5-oxo-2-imidazolin-2-yl)-7-quinolinecarboxylate | .500 | 0 | 0 | 0 | 0 | 0 | 0 | 0 | 4 | 0 | 0 | 0 |
|  | .250 | 0 | 0 | 0 | 0 | 0 | 0 | 0 | 1 | 0 | 0 | 0 |
| 5-(4-Isopropyl-4-methyl-5-oxo-2-imidazolin-2-yl)-6-quinoxalinecarboxylic acid | .500 | 0 | 0 | 0 | 0 | 4 | 0 | 0 | 4 | 2 | 0 | 0 |
|  | .250 | 0 | 0 | 0 | 0 | 0 | 0 | 0 | 1 | 0 | 0 | 0 |
| 3,4-Dihydro-7(and 6)-(4-isopropyl-4-methyl-5-oxo-2-imidazolin-2-yl)-1H-2-benzopyran-6(and 7)-carboxylic acid, 1:1 mixture | 2.000 | 5 | 6 | 4 | 3 | 9 | 9 | 2 | 6 | 5 | 3 | — |
|  | 1.000 | 1 | 1 | 0 | 1 | 7 | 0 | 1 | 6 | 4 | 1 | — |

EXAMPLE 25

Postemergence Herbicidal Evaluation of Test Compounds

The postemergence herbicidal activity of the imidazolinyl benzoheterocyclic compounds of the present invention is demonstrated by the following tests wherein a variety of monocotyledenous and dicotyledenous plants are treated with solutions of the test compound in aqueous acetone. Said test solutions consist of a 50/50 acetone/water mixture containing 0.5%

TWEEN 20, a polyoxyethylene sorbitan monolaurate surfactant manufactured by Atlas Chemical Industries and a test compound in sufficient quantity to provide the equivalent of about 0.016 kg/ha to 1.00 kg/ha of active compound when applied to the plants through a spray nozzle operating at 40 psi for a predetermined time. In the tests, seedling plants are grown in jiffy flats for about 2 weeks. The plants are sprayed with the test solution, placed on greenhouse benches and cared for in the usual manner commensurate with conventional greenhouse practice.

From 4 to 5 weeks after treatment, the plants are examined and rated according to the rating system described hereinabove. The herbicidal effectiveness of the compounds of the present invention is evident from the data recorded in Table II below.

When more than one test is performed for a given compound, the data are averaged.

PLANT SPECIES USED

| Header Abb | Common Name | Scientific Name |
|---|---|---|
| Barnyardgr | Barnyardgrass | *Echinochloa crus-galli*, (L) Beau |
| Foxtail Sp | Foxtail Spp. | *Setaria* Spp. |
| P Nutsedge | Nutsedge, Purple | *Cyperus rotundus*, L. |
| Wild Oats | Oat, Wild | *Avena fatua*, L. |
| Quackgrass | Quackgrass | *Agropyron repens*, (L) Beauv. |
| Fld Bindwd | Bindweed, Field (Rhizome) | *Convolvulus arvensis*, L. |
| Mrnglry Sp | Morningglory Spp. | *Ipomoea* Spp. |
| Wild Mustd | Mustard, Wild | *Brassica kaber*, (DC) L. C. Wheelr |
| Velvetleaf | Velvetleaf | *Abutilon theophrasti*, Medic. |
| Wht Fenman | Wheat, Fenman | *Triticum aestivum*, Fenman |
| Soybean Br | Soybean, Bragg | *Glycine*, max (L) Men. CV Bragg |

TABLE II

| | | Postemergence Herbicidal Evaluation | | | | | | | | | |
|---|---|---|---|---|---|---|---|---|---|---|---|
| Compound Name | Rate Kg/ha | Barny ardgr | Foxta il Sp | P Nut sedge | Wild Oats | Quack grass | Fld Bl ndwd | Mrngl ry Sp | Wild Mustd | Velve tleaf | Wht F enman | Soybe an Br |
| 8-(4-Isopropyl-4-methyl-5-oxo-2-imidazolin-2-yl)-7-quinolinecarboxylic acid | 1.000 | 4 | 7 | 4 | 2 | 0 | 9 | 8 | 9 | 2 | 0 | 0 |
| | .500 | 1 | 2 | 2 | 0 | 0 | 9 | 8 | 9 | 0 | 0 | 0 |
| | .250 | 0 | 2 | 2 | 0 | 0 | 9 | 8 | 9 | 0 | 0 | 0 |
| Methyl 8-(4-isopropyl-4-methyl-5-oxo-2-imidazolin-2-yl)-7-quinolinecarboxylate | 1.000 | 0 | 0 | 0 | 0 | 0 | 7 | 0 | 8 | 0 | 0 | 0 |
| | .500 | 0 | 0 | 0 | 0 | 0 | 4 | 0 | 4 | 0 | 0 | 0 |
| 3,4-Dihydro-7(and 6)-(4-isopropyl-4-methyl-5-oxo-2-imidazolin-2-yl)-1 H-2-benzopyran-6(and 7)-carboxylic acid, 1:1 mixture | 2.000 | 0 | 9 | 0 | 0 | 0 | 0 | 0 | 7 | 0 | 0 | 0 |
| | 1.000 | 0 | 6 | 0 | 0 | 0 | 0 | 0 | 7 | 0 | 0 | 0 |

What is claimed is:
1. The compound 8-(4-isopropyl-4-methyl-5-oxo-2-imidazolin-2-yl)-7-quinolinecarboxylic acid.

* * * * *